United States Patent
Kato et al.

(10) Patent No.: US 7,434,437 B2
(45) Date of Patent: Oct. 14, 2008

(54) METHOD OF MAKING A METALLIC THIN WIRE FOR A MEDICAL TOOL

(75) Inventors: Tomihisa Kato, Aichi-ken (JP); Kenji Miyata, Aichi-ken (JP)

(73) Assignee: Asahi Intec Co., Ltd., Nagoya-shi (JP)

( * ) Notice: Subject to any disclaimer, the term of this patent is extended or adjusted under 35 U.S.C. 154(b) by 160 days.

(21) Appl. No.: 11/398,584

(22) Filed: Apr. 6, 2006

(65) Prior Publication Data

US 2006/0179909 A1  Aug. 17, 2006

Related U.S. Application Data

(62) Division of application No. 10/874,756, filed on Jun. 24, 2004.

(30) Foreign Application Priority Data

Jun. 26, 2003  (JP) ............................... 2003-181956

(51) Int. Cl.
 *B21D 11/14* (2006.01)
(52) U.S. Cl. .......................................... 72/299; 72/371
(58) Field of Classification Search ................... 72/299, 72/371; 140/147
See application file for complete search history.

(56) References Cited

U.S. PATENT DOCUMENTS

| | | | | |
|---|---|---|---|---|
| 2,352,442 | A | * 6/1944 | Ludwig et al. | ................. 72/299 |
| 3,677,309 | A | * 7/1972 | Grandy | ........................ 140/149 |
| 5,637,089 | A |   6/1997 | Abrams et al. | ................. 604/95 |
| 5,676,013 | A | * 10/1997 | Kahlau | ........................ 72/299 |
| 5,956,935 | A | *  9/1999 | Katayama et al. | ............. 57/212 |
| 6,009,738 | A | *  1/2000 | Beecher et al. | ................ 72/299 |
| 6,042,553 | A |    3/2000 | Solar et al. | ................... 600/585 |
| 6,068,623 | A |    5/2000 | Zadno-Azizi et al. | ........ 604/530 |
| 6,168,571 | B1 |   1/2001 | Solar et al. | ................... 600/585 |
| 6,287,292 | B1 |   9/2001 | Fariabi | ........................ 604/531 |
| 6,508,803 | B1 |   1/2003 | Horikawa et al. | ........... 604/523 |
| 6,702,842 | B2 | *  3/2004 | Dobak et al. | ................. 607/105 |
| 6,729,026 | B2 | *  5/2004 | Garcia et al. | ................... 29/882 |
| 2004/0023186 | A1 | * 2/2004 | McSpadden | ................ 433/102 |

FOREIGN PATENT DOCUMENTS

| | | |
|---|---|---|
| GB | 1119158 | 7/1968 |
| JP | 07-148267 | 6/1995 |
| JP | 2000-512691 | 9/2000 |
| WO | WO 03/039623 A2 | 5/2003 |

* cited by examiner

*Primary Examiner*—Daniel C Crane
(74) *Attorney, Agent, or Firm*—Morgan, Lewis & Bockius LLP

(57) ABSTRACT

In a method of making a metallic thin wire 1, one single metallic thin wire 2 is prepared to have a predetermined length with a middle portion of the one single metallic thin wire 2 as a fixed portion. Front and rear half portions of the one single metallic thin wire 2 are twisted with a tensile weight W applied to the front and rear half portions in the lengthwise direction. The one single metallic thin wire 2 is processed with a heat treatment to remove a residual stress. This provides the metallic thin wire 1 with a high rotation-following capability and high torque transmissibility, thus enabling artisans to usefully apply the metallic thin wire 1 to a main wire component 25 of a medical tool and equipment.

4 Claims, 7 Drawing Sheets

METHOD OF MAKING A METALLIC THIN WIRE FOR A MEDICAL TOOL

This is a divisional application of copending application Ser. No. 10/874,756, filed on Jun. 24, 2004, which is hereby incorporated by reference.

BACKGROUND OF THE INVENTION

1. Filed of the Invention

The invention relates to a method of making a metallic thin wire in the form of a flexible wire configuration used as a main wire component of a medical tool such as a catheter, a catheter guide wire, an endscope treating instrument or the like.

2. Description of Prior Art

In a catheter and a catheter guide wire which introduces a leading distal end into a diseased area through a sinuous vascular system, the leading distal end of the catheter or the catheter guide wire is inserted into the blood vessel or the somatic cavity by a "push-pull and turn" manipulation at a hand access portion located outside a subject patient upon treating the diseased area. In an endscope treating instrument which is inserted through a somatic cavity to reach the diseased area, a leading end of the endscope treating instrument is manipulated in the same manner as mentioned above.

In order to achieve a smooth manipulation when inserting the leading distal end into the somatic cavity and the blood vessel, it is required for these medical devices to have multi-mechanical properties. The multi-mechanical properties include a high flexibility, a good straightness and restitutivity in an unrestricted free state against bending deformation. The medical devices of these types are required at its leading distal end portion to have a high flexibility, while at the same time, required at its rear portion to have an appropriate rigidity as a functionally gradient property. It is also indispensable for the leading distal end to have a good maneuverability in which the leading distal end properly responds to the hand operation conducted outside the subject patient.

The following publications disclose flexible linear wires used as a main component of the medical devices with an aim to achieving the above indispensable multi-mechanical properties.

In the references of Laid-open Japanese Patent Application No. 7-148267 and Domestic Publication No. 2000-512691 (referred in turn to as "first and second reference" hereinafter), the first reference shows a method of making a metallic thin wire in which a metallic wire is mechanically rolled straight through a correction roller, and then thermally treated to remove a residual stress so as to produce a medical guide wire superior in linearity and straightness.

The second reference also shows a method of making a metallic thin wire in which a thin wire is made of a shape-memory alloy, and twisted under a tensile force applied to the thin wire, and then thermally treated to remove a residual stress so as to produce a catheter guide wire.

The medical guide wire produced by the first reference is superior in a lengthwisely directed straightness. It is, however, poor in torsional characteristics. This leads to a shortage of the torque transmissibility and rotational maneuverability so as to reduce a good steerability.

The catheter guide wire produced by the second reference specifies the shape-memory alloy, and only one metallic thin wire is prepared each time the method is used upon producing the catheter guide wire. This makes the catheter guide wire costly and disadvantageous especially when brought to the mass production. In addition, the metallic thin wire is twisted only in one direction, and thus making the torsional characteristics uneven in the lengthwise direction. Because the metallic thin wire is twisted only in one direction, and not twisted further in another direction, the metallic thin wire becomes to lose the torque transmissibility and rotation-following capability so as to reduce the steerability when applied to the medical guide wire, and maneuvered to swivel the guide wire in the right and left directions upon inserting the guide wire into the vascular vessel.

Therefore, it is an object of the invention to overcome the above drawbacks so as to provide a method of making a metallic thin wire for a medical tool which are capable of improving a rotation-following capability and torque transmissiblity so as to enhance a steerability.

According to the present invention, there is provided a method of making a metallic thin wire which is twisted in one direction under a tensile weight applied in the lengthwise direction, or primarily and secondarily twisted alternately in one direction and the opposite direction under the tensile weight applied in the lengthwise direction. This induces a uniform torsional rigidity in the right and left directions through an entire length of the one single metallic thin wire.

According to other aspect of the present invention, one single metallic thin wire is prepared to have a predetermined length or a bifold extension of the predetermined length. A middle portion of the one single metallic thin wire is fixedly supported at a fixed portion. Front and rear half portions of the one single metallic thin wire is twisted (in one direction) with the front and rear half portions symmetrically located at both sides of the fixed portion. At the time of twising the front and rear half portions, a tensile weight is concurrently applied to the front and rear half portions. This produces two metallic thin wires simultaneously in a dual-way fashion to maintain the product quality uniform, while at the same time, improving the productivity.

According to other aspect of the present invention, the one single metallic thin wire which is primarily twisted is further twisted secondarily. At the time of primarily twisting the one single metallic thin wire, the one single metallic thin wire is excessively twisted nearly to induce slip lines (Lüder's lines) on an outer surface of the one single metallic thin wire. Total turning times of the secondarily twisting step is more than 0.15 times of that of the primarily twisting step, but less than 1.5 times of that of the primarily twisting step. It is preferable that the primarily twisting numbers of times is 0.2 times as great as that of the secondarily twisting numbers of times.

The one single metallic thin wire is divided into a plurality of zones in the lengthwise direction, each of which is twisted in different number of turns, or processed with the heat treatment in varied degrees so as to enhance the performance when the one single metallic thin wire is applied to a medical tool or equipment. From the same viewpoint, an outer surface of the one single metallic thin wire is treated with an electrolytic polishing procedure. Alternatively, the one single metallic thin wire is made of an austenitic stainless steel.

The metallic thin wire thus produced is applied to a main wire element, a shaft, a stylus, a pull-wire, a stent and a needle in the medical tools such as, for example, a catheter, a balloon catheter and a medical endscope.

From the viewpoint of an operation and advantages of the present invention, the one single metallic thin wire is twisted in one direction or primarily and secondarily twisted alternately under the lengthwise tensile weight. This reduces a torsional elasticity to impart the one single metallic thin wire with an enhanced torsional rigidity. When the one single metallic thin wire is primarily and secondarily twisted alternately, the uniform torsional rigidity develops in the right and left directions through an entire length of the one single metallic thin wire.

By primarily twisting the one single metallic thin wire excessively beyond the yield point, a slipping stress prevails through the entire length to induce wavy slip lines (Lüider's lines) on the weak portion of the one single metallic thin wire so as to equalize the torsional characteristics through the entire length of the one single metallic thin wire. By secondarily twisting the one single metallic thin wire after primarily twisted, the excessive amount of the twisted turns is retrieved to a certain degree, and then the one single metallic thin wire is processed with the heat treatment to remove the residual stress. This imparts the metallic thin wire with a highly improved linearity and straightness.

When the one single metallic thin wire is processed with the heat treatment while excessively twisted only in one direction, the one single metallic thin wire is likely to torsionally and wavily deform due to the reaction force developed from excessively twisting the one single metallic thin wire.

When the one single metallic thin wire is processed with the heat treatment while not excessively twisted in one direction, the one single metallic thin wire is likely to become bendable, although the heat treatment decreases the torsional and wavy deformation, to which the one single metallic thin wire is subjected.

In general, the one single metallic thin wire has a tendency to develop the torsional and wavy deformation due to an unevenness between one portion in which an elastic reaction develops against the torsional direction and other portion in which a plastic deformation starts to appear when the one single metallic thin wire is twisted with one end of the thin wire as a fixed portion.

In the present invention, the one single metallic thin wire is primarily and secondarily twisted alternately in mutually opposed directions. This makes the resultant numbers of twisting turns uniform with a high torsional rigidity due to a total sum of the twisting turns in the right and left directions when taking the primarily and secondarily twising numbers plus and minus respectively.

The one single metallic thin wire is primarily and secondarily twisted alternately under the tensile weight applied to the one single metallic thin wire, and then processed with the heat treatment to remove the residual stress.

This produces the metallic thin wire highly superior in the rotation-following capability (torsional rigidity and torque transmissibility) in both the right and left directions while securing a high flexibility and linearity in the one single metallic thin wire.

For a medical tool and equipment into which the metallic thin wire is incorporated as the main wire component, the present method enables the main wire component to a highly superior rotation-following capability (torsional rigidity and torque transmissibility) so as to enhance the performance depending on its usage.

BRIEF DESCRIPTION OF THE DRAWINGS

A preferred form of the present invention is illustrated in the accompanying drawings in which.

DETAILED DESCRIPTION OF PREFERRED EMBODIMENTS OF THE INVENTION

Figure 1:
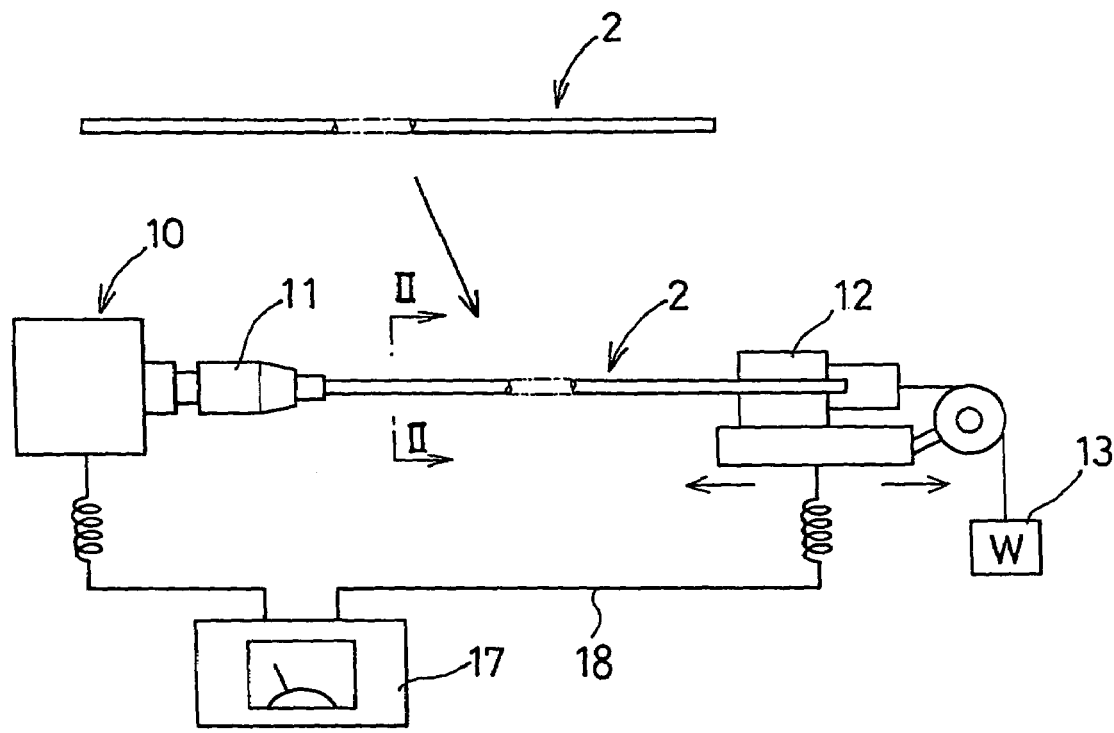
FIG. 1 is an explanatory view of one single metallic thin wire attached to a twisting device to explain a method of twisting the one single metallic thin wire according to a first embodiment of the invention.

In the following description of the depicted embodiments, the same reference numerals are used for features of the same type.

Figure 13:
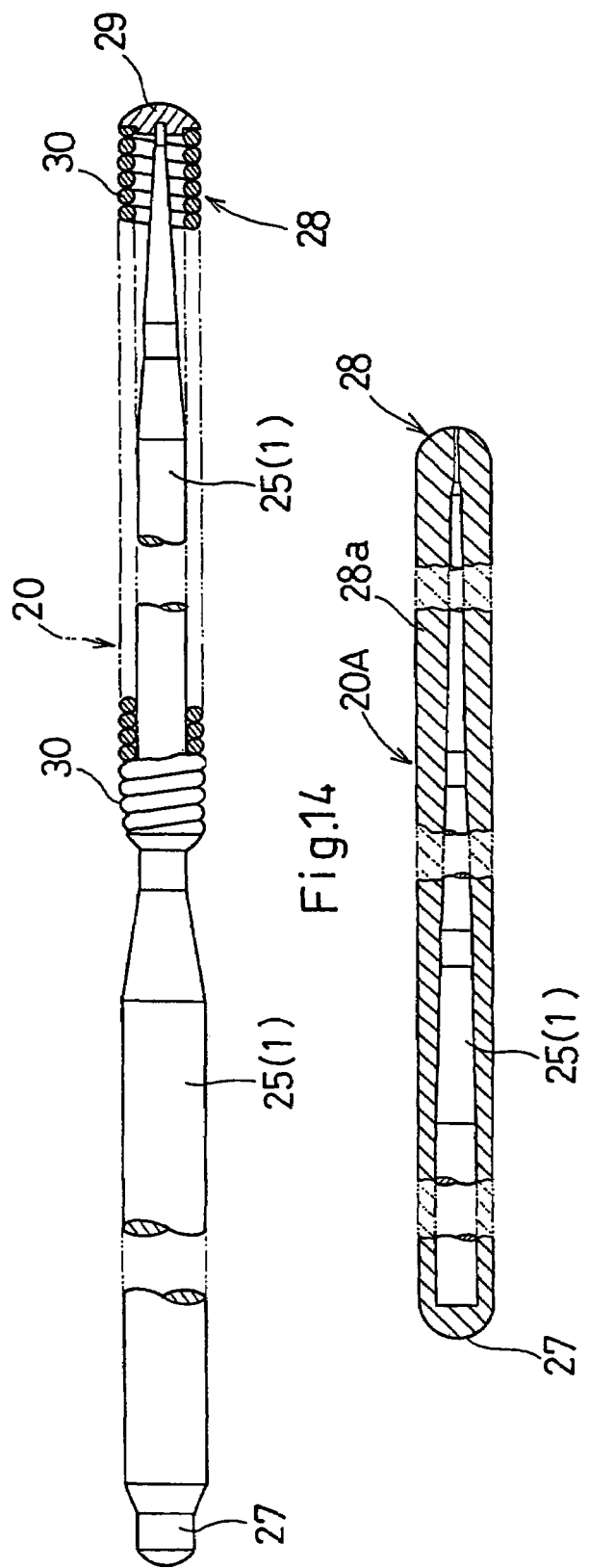
FIG. 13 is a plan view of a medical guide wire into which the metallic thin wire is incorporated as a main wire component according to a fifth embodiment of the invention, but partly cross sectioned.
Figure 14:
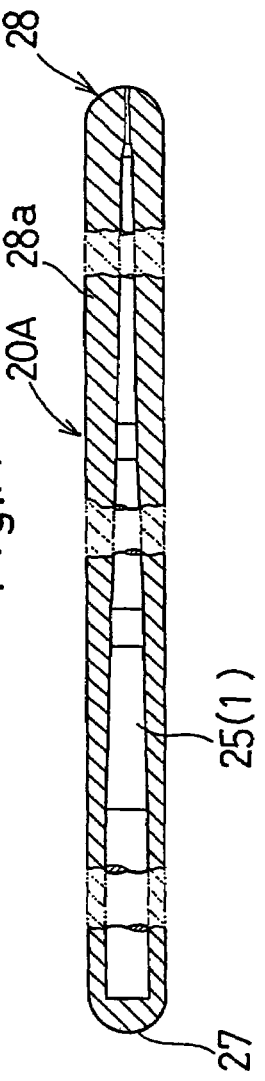
FIG. 14 is a longitudinal cross sectional view of a medical guide wire into which the metallic thin wire is incorporated as a main wire component according to a sixth embodiment of the invention.
Figure 15:
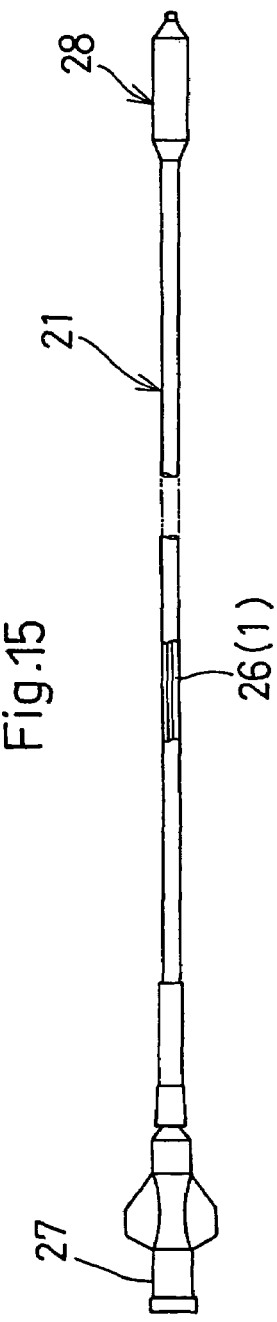
FIG. 15 is a plan view of a balloon catheter into which the metallic thin wire is incorporated as a main wire component according to a seventh embodiment of the invention.

Referring to FIGS. 1 through 4, a method of making a metallic thin wire 1 is described according to a first embodiment of the invention. The metallic thin wire 1 is employed to a main wire component of a medical guide wire 20 (20A) and a balloon catheter 21 as shown in FIGS. 13 through 15. As a raw material of the metallic thin wire 1, one single metallic thin wire 2 (referred merely to as "thin wire 2" hereinafter) is drawn and severed to have a predetermined length and diameter as shown in FIG. 1. By way of illustration, the thin wire 2 is made of an austenitic stainless steel, and attached to a twisting device 10 to be twisted and processed with a heat treatment to remove a residual stress as described hereinafter.

The thin wire 2 has a predetermined length (e.g., 1.000-1.500 mm), one end of which is firmly clamped by a rotary chuck 11. The other end of the thin wire 2 is clamped by a slidable chuck 12 which is provided slidably in a lengthwise direction. The slidable chuck 12 has a tensile weight W which hangs down a static load 13 to apply a tensile weight W to the thin wire 2 in its stretchy direction. This brings the thin wire 2 straight to the stretch between the rotary chuck 11 and the slidable chuck 12 with the tensile weight W as a torsion-resistant load. Across the rotary chuck 11 and the slidable chuck 12, an electrically conductive line 18 is connected to be energized by a current generator 17. With the energization of the current generator 17, the electric current flows through the thin wire 2 to thermally treat the thin wire 2 by its electric resistance.

Figure 2:
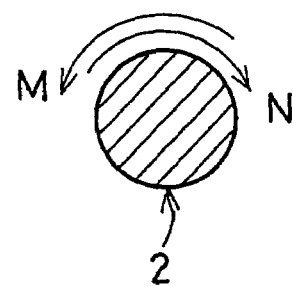
FIG. 2 is a latitudinal cross sectional view taken along the line II-II of FIG. 1.

With the thin wire 2 thermally treatable under the tensile weight W, the thin wire 2 is primarily twisted about its axis in the direction as shown at an arrow M in FIG. 2. Then, the thin wire 2 is secondarily twisted in the direction to return the way which the thin wire 2 is primarily twisted. As shown at an arrow N in FIG. 2, the secondarily twisted direction is opposite to the direction in which the thin wire 2 is primarily twisted.

Concurrently with the secondarily twisting the thin wire 2 or after the secondarily twisting the thin wire 2, the thin wire 2 is processed with the heat treatment due to the electric resistance to remove the residual stress from the thin wire 2. This process enables the metallic thin wire 1 to a highly superior rotation-following capability and linearity as shown in FIG. 3.

After the end of the heat treatment, the metallic thin wire 1 is treated at its outer surface with an electrolytic polishing procedure so as to be consecutively produced as the main wire component 25 of the medical guide wire 20 for the purpose of mass production.

By way of example, an outer diameter of the main wire component 25 measures 0.342 mm, the primarily twisting numbers of times is 125-185, the secondarily twisting numbers of times is 18-280, the electric current employed herein is for 3-5 minutes at 2.0-2.3 ampere, and the tensile weight W measures 4-6 kg as the torsion-resistant load.

Figure 3:
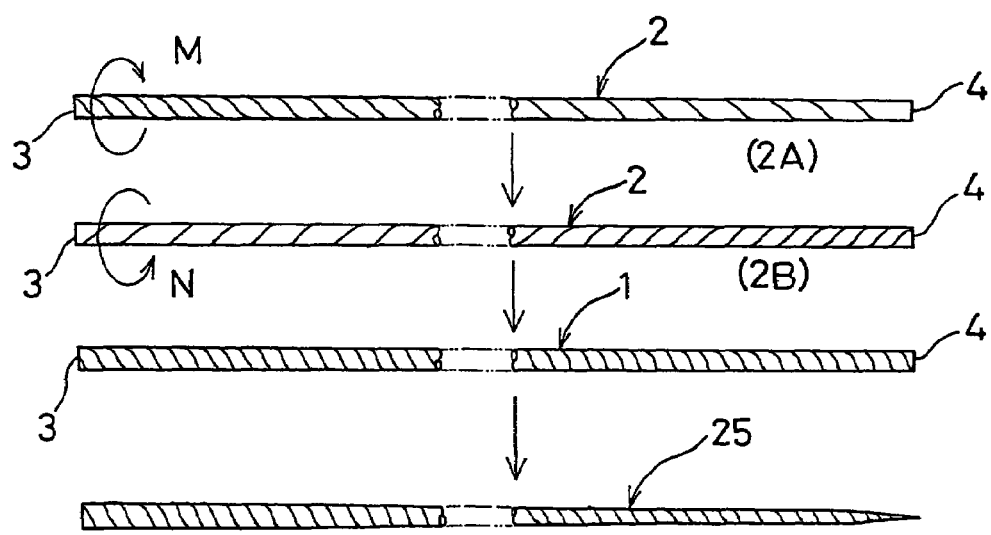
FIG. 3 is an explanatory view showing how the one single metallic thin wire is twisted.

The primarily twisted thin wire 2 progressively decreases its twisted numbers of times from one side 3 of the rotary chuck 11 to the other side 4 of the slidable chuck 12 as shown at an initial metamorphous stage 2A in FIG. 3. At the time of secondarily twisting the thin wire 2 with the primarily twisted condition maintained, the secondarily twisted thin wire 2 influences its own twisted numbers of times to successively increase from one side 3 of the rotary chuck 11 to the other side 4 of the slidable chuck 12 as shown at a subsequent metamorphous stage 2B in FIG. 3.

Based on the composite metamorphosis of the thin wire 2 primarily and secondarily twisted and a total sum of the primarily and secondarily twisted numbers of times, the thin wire 2 comes to be equally twisted substantially through the entire length of the thin wire 2. By primarily and secondarily twisting the thin wire 2 alternately, a torsional rigidity is induced on the thin wire 2 equally in its lengthwise direction to impart the thin wire 2 with a uniform rotation-following capability and linearity substantially through the entire length of the thin wire 2. Wavy curves depicted on the metallic thin wire 1, the thin wire 2 and the main wire component 25 in FIG. 3 are for the purpose of clarifying unrecognizable marks on each wire element.

Figure 4:
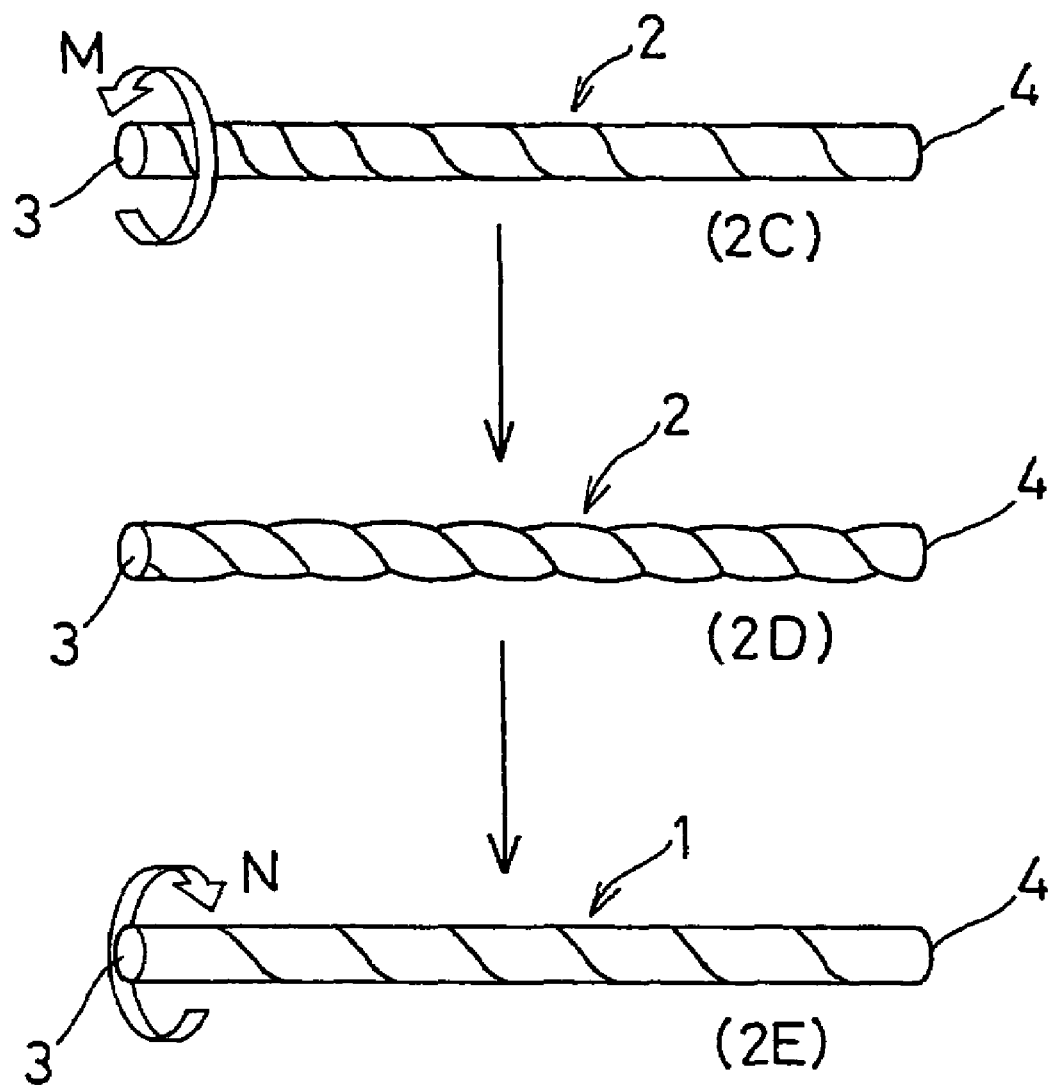
FIG. 4 is an explanatory view showing how an outer surface of the one single metallic thin wire changes as the one single metallic thin wire is twisted.
Figure 5:
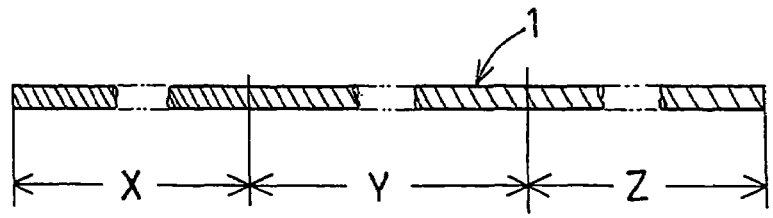
FIG. 5 is an explanatory view showing how one single metallic thin wire is twisted into a metallic thin wire according to a second embodiment of the invention.
Figure 6:
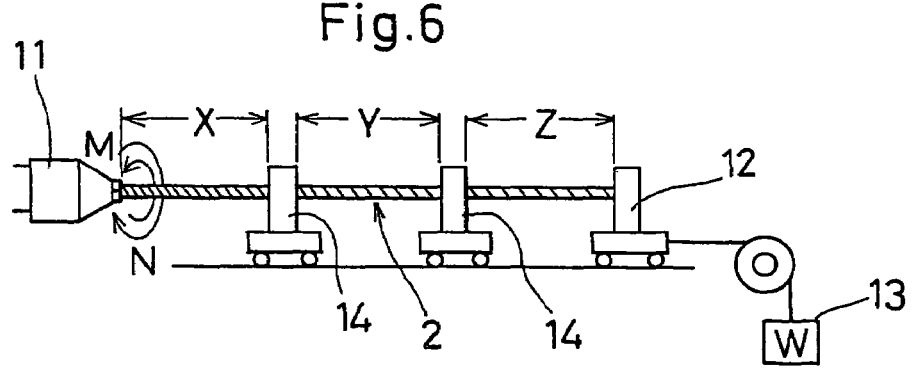
FIG. 6 is an explanatory view of a twisting device on which the one single metallic thin wire is mounted to be twisted.

More particularly, during primarily twisting the thin wire 2, a torsional surface appears on the thin wire 2 as shown at stage one 2C in FIG. 4. At the end of the primarily twisting (excessive twist) the thin wire 2, a swollen surface appears on the thin wire 2 with a torsional pitch maintained substantially uniform as shown at stage two 2D in FIG. 4. At the end of the secondarily twisting the thin wire 2, the swollen surface disappears from the thin wire 2 with the torsional pitch somewhat larger than that of the stage two 2D as shown at stage three 2E in FIG. 4. The non-swollen surface runs in a spiral fashion with the lead angle as 4-5 degrees. In this instance, the stage three 2E is in the condition in which the primarily twisted numbers of times is approximately 20% of the secondarily twisted numbers of times.

FIGS. 5 through 8 show a second embodiment of the invention in which the thin wire 2 is divided into a plurality of zones X, Y and Z in the lengthwise direction. The zones X, Y and Z in turn have different twisted numbers of times after the thin wire 2 is primarily and secondarily twisted depending on the zones X, Y and Z. When the thin wire 2 is used to the medical guide wire 20, 20A and the balloon catheter 21 as shown in FIGS. 13 through 15, the zone X has the largest numbers of twisted times to position near a hand access portion 27 with the smallest numbers of twisted times given to the zone Z. The zone Y, which positions between the zone X and the zone Z, has a middle numbers of twisted times between the largest and smallest numbers of twisted times. In this way, the thin wire 2 are wrought out to have the different numbers of twisted times discretely depending on the zones X, Y and Z.

Figure 7:
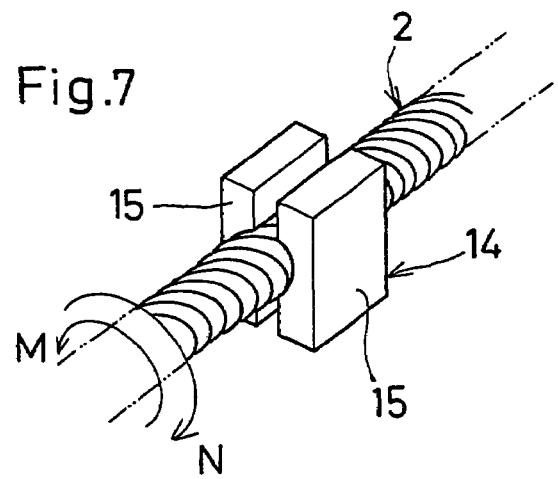
FIG. 7 is a perspective view showing how an intermediary clamp device works in the twisting device.

In the second embodiment of the invention, an intermediary clamp device 14 is slidably placed between the rotary chuck 11 and the slidable chuck 12 in the twisting device 10 as shown in FIG. 7. The clamp device 14 has a pair of movable clamp pieces 15 to clamp the thin wire 2 at an appropriate position. The clamp device 14 is placed at boundaries between the zones X, Y and Z to clamp the boundaries in turn with a predetermined time lag at the time when primarily and secondarily twisting the thin wire 2. This enables artisans to produce the zones X, Y and Z of different numbers of twisted times.

Figure 8:
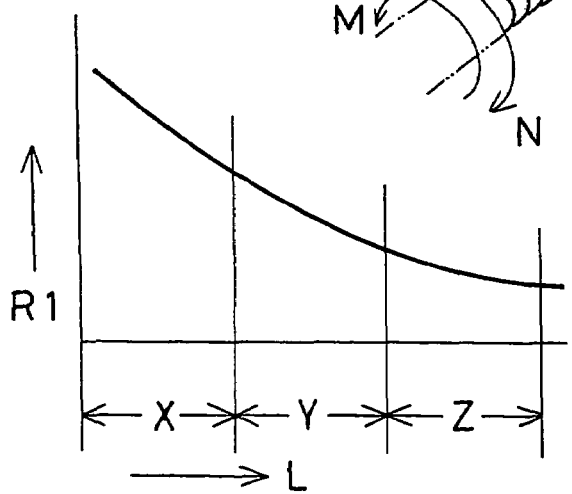
FIG. 8 is a graphical representation characteristic of the metallic thin wire.

The thin wire 2 thus provided has a mechanical property in which a bending characteristics differs hard and soft depending on the zones X, Y and Z as shown in FIG. 8. When the thin wire 2 is applied as a flexible line wire to the medical guide wire 20, 20A and the balloon catheter 21 (medical tools), the thin wire 2 progressively changes its bending rigidity R1 along the lengthwise direction L so as to produce the high quality metallic thin wire 1, the rigidity and flexibility of which gradually change to represent a functionally gradient characteristics.

Namely, the most rigid portion of the medical tools is a place in which the hand access portion 27 positions to be grasped and maneuvered outside the subject patient. The most flexible portion of the medical tools is a leading head portion to be inserted into the blood vessel and somatic body.

Figure 9:
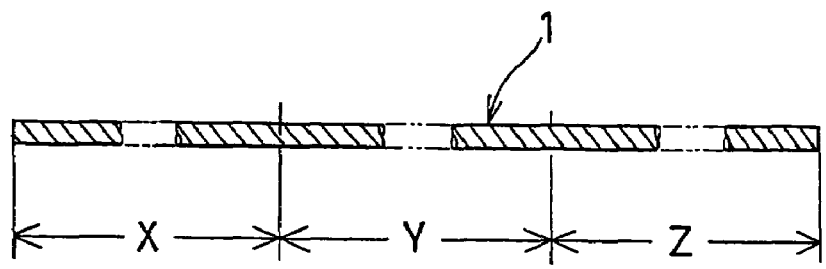
FIG. 9 is an explanatory view showing how one single metallic thin wire is twisted into a metallic thin wire according to a third embodiment of the invention.
Figure 10:
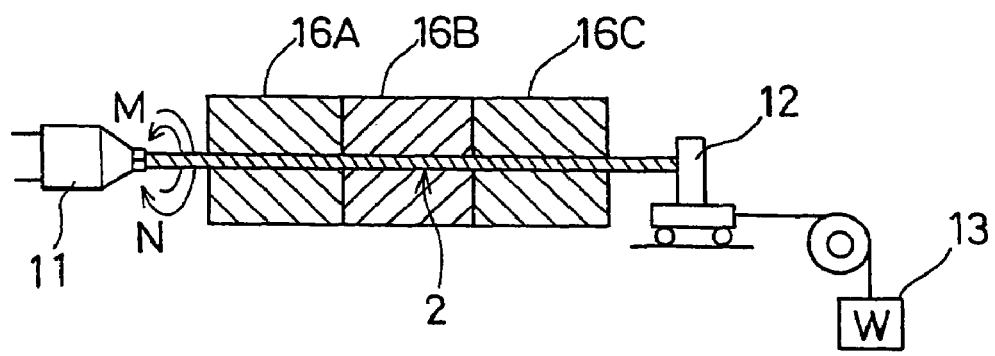
FIG. 10 is an explanatory view of the one single metallic thin wire mounted on the twisting device to explain the method of twisting the one single metallic thin wire.
Figure 11:
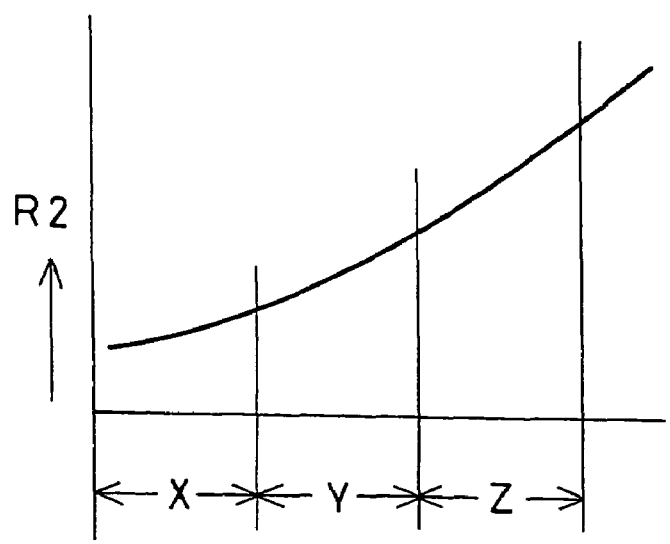
FIG. 11 is a graphical representation characteristic of the metallic thin wire.

FIGS. 9 through 11 show a third embodiment of the invention in which the thin wire 2 is divided into a plurality of zones X, Y and Z in the lengthwise direction. The zones X, Y and Z have heating devices 16A, 16B and 16C in turn to be heated in different degrees depending on the zones X, Y and Z after the thin wire 2 is primarily and secondarily twisted into the metallic thin wire 1. The residual stress is removed from the thin wire 2 in varied degrees depending on the zones X, Y and Z. For this reason, the thin wire 2 has a tensile strength and bending rigidity R2 gradually changing in the lengthwise direction L as shown in FIG. 11. This enables the metallic thin wire 1 to work as a high quality main wire component for the medical guide wire 20, 20A and the balloon catheter 21.

In this instance, any of the metallic thin wire 1 can be used which represents the first and second embodiment of the invention.

Figure 12:
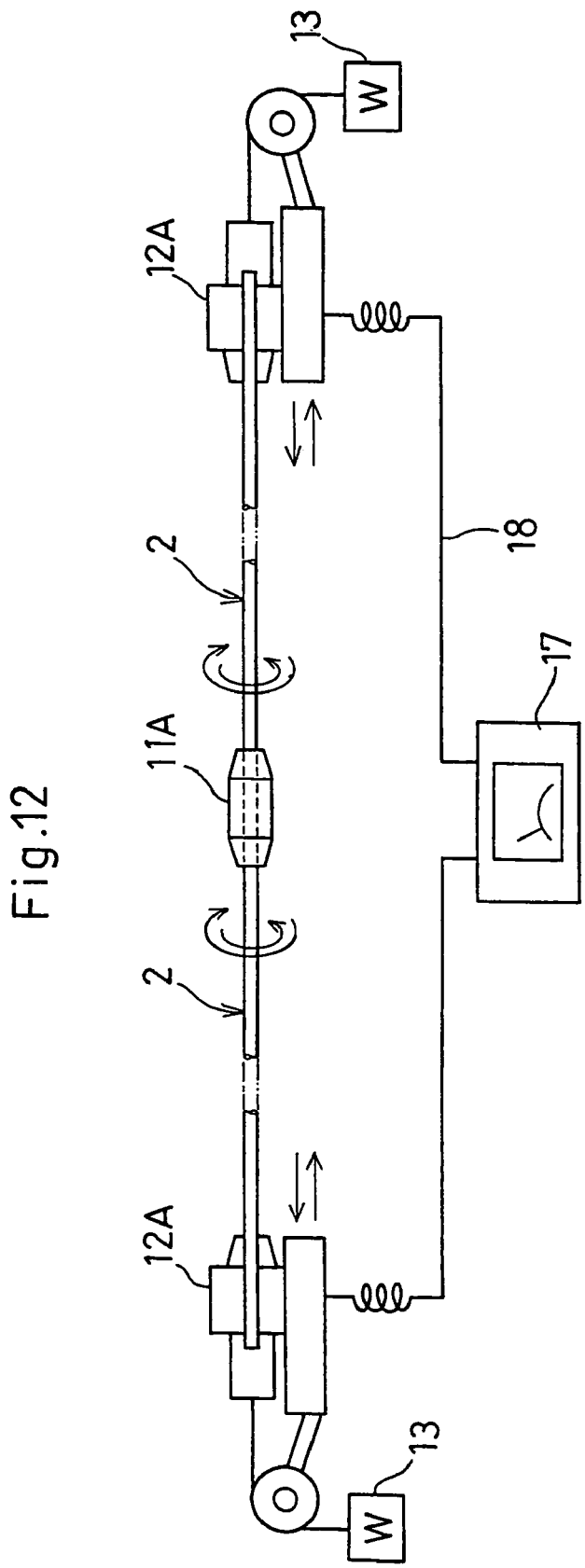
FIG. 12 is an explanatory view showing how a metallic thin wire is manufactured according to a fourth embodiment of the invention.

FIG. 12 shows a fourth embodiment of the invention in which a dual rotary chuck 11A is provided in the twisting device 10. An extension of the thin wire 2 is a bifold of the predetermined length. A middle section of the thin wire 2 is firmly clamped by the dual rotary chuck 11A. Both ends of the thin wire 2 is clamped by a slidable chuck 12A which hangs down the tensile weight W.

In this instance, the thin wire 2 symmetrically locates its right (front) half portion and left (rear) half portion in a dual fashion. Thereafter, the right and left half portions are primarily and secondarily twisted in the same manner as done in the first embodiment of the invention. With the use of the dual rotary chuck 11A, two metallic thin wires can be produced concurrently, thus reducing the manufacturing cost with a high productivity. The two metallic thin wires are produced under the same conditions, thus contributing to equalizing the quality of the product.

FIG. 13 shows a fifth embodiment of the invention in which the metallic thin wire 1 is used to the medical tool and equipment. In this instance, the metallic thin wire 1 is made of the austenitic stainless steel and produced by any of the method described from the first embodiment to the fourth embodiment of the invention. The metallic thin wire 1 thus produced is applied as the main wire component 25 to the medical guide wire 20.

FIG. 14 shows a sixth embodiment of the invention in which the metallic thin wire 1 is used to the medical tool. The metallic thin wire 1, which is produced in the same manner as done in the fifth embodiment of the invention, is applied as the main wire component 25 to the medical guide wire 20A which is structurally different from the previous medical guide wire 20. An entire surface of the main wire component 25 is coated with such as, for example, a polyamide (Nylon 66) layer 28a which contains a contrast medium (e.g., barium sulfate).

FIG. 15 shows a seventh embodiment of the invention in which the metallic thin wire 1 is used to the medical tool and equipment. In this instance, the metallic thin wire 1 is made of the austenitic stainless steel and produced by any of the method described from the first embodiment to the fourth embodiment of the invention. The metallic thin wire 1 thus produced is applied as a shaft 26 to the balloon catheter 21.

This results in the guide wire 20, 20A and the balloon catheter 21 having a transmissible elongation made of the thin metallic wire 1 to transmit a manipulation from the hand access portion 27 to the leading head portion 28. This enables the hand access portion 27 to transmit its push-pull and rotational movement in quick response to the leading head portion 28 with a high accuracy. This ensures a good maneuverability of the guide wire 20, 20A and the balloon catheter 21 so as to secure a quicker remedial treatment against the diseased area.

When the metallic thin wire 1 is wrought out to have the functionally gradient characteristics as done in the second and third embodiments of the invention, and the metallic thin wire 1 is applied to the main wire component 25 of the guide wire 20, 20A, the functionally gradient characteristics makes the hand access section 27 flexible, while at the same time, making the rigid leading head portion 28 hard, thus significantly improving the mechanical property as required for the guide wire 20, 20A.

In addition, the metallic thin wire 1 made of the austenitic stainless steel as described from the fifth to seventh embodiments of the invention has the following advantages as the guide wire 20, 20A.

When a martensitic stainless steel is used to the main wire component 25 as shown in FIG. 13, it tends to harden with the heat treatment so as to likely make a helical portion 30 and the main wire component 25 partly stiffen in the neighborhood of the bulge head portion 29 under the thermal influence produced at the time of soldering the bulge head portion 29, thereby resultantly depriving the leading head portion 28 of the favorable flexibility.

On the other hand, a ferritic stainless steel has the property referred to as "475° C. fragility" and having the property called as "sigma fragility" occurred when heated to approx. 600-800° C. for an extended period of time. Especially, the ferritic stainless steel makes the crystallized particles grow to reveal "high temperature frailty" when heated to 950° C. or more, thereby deteriorating the quality as the medical guide wire due to the thermal influence brought by thermally bonding the bulge head portion 29.

However, since the austenitic stainless steel is less subjected to the textural metamorphosis when heated, it is less affected by the heat generated at the time of thermally bonding the bulge head portion 29. The austenitic stainless steel further has a relatively small thermal conductivity and a greater coefficient of thermal expansion which is approx. 1.5-1.6 times as large as that of the general stainless steel. This means that the thermal expansion and the thermal stress produced on the main wire component 25 by thermally bonding the bulge head portion 29 are absorbed by a limited area of the main wire component 25 in the neighborhood of the bulge head portion 29. This alleviates the residual stress produced by thermally bonding the bulge portion 29, and thereby maintaining the good linearity and favorable flexibility even in the restricted portion of the main wire component 25 near the bulge head portion 29.

The thin wire 2 contracts and stretches in the lengthwise direction when primarily and secondarily twisted alternately and then processed with the heat treatment. Due to the greater coefficient of thermal expansion of the austenitic stainless steel, a stroke appeared when the thin wire 2 contracts and stretches becomes longer to work out the outer surface of the thin wire 2 to help it form a closely packed structure.

While on the other hand, the martensitic stainless steel has a quench hardening property by which a tensile strength is reinforced, the austenitic stainless steel increases its strength when drawn (work hardening) so as to be well-suited to the medical guide wire 20, 20A. Since an electric resistance of the austenitic stainless steel is approx. five times as great as that of the carbon steel, and is approx. 1.6 times as great as that of the martensitic stainless steel. This alleviates an intensity of the electric current necessary to thermally bond the bulge head portion 29, whereby limiting the thermally bonding heat to a necessary minimum so as to lessen a bending and torsional deformation under the influence of the heat generated by thermally bonding the bulge head portion 29.

With the thin wire 2 specified by the austenitic stainless steel, the thin wire 2 is magnetized and mirror-finished at its outer surface when drawn by a dice tool. This attracts ferric particles to the outer surface of the thin wire 2 and collects foreign matters on the thin wire 2 with the help of the Van del Waals' force based on the intermolecular affinity. When the foreign matters are collected, the passive rust corrosion and the crevice corrosion would occur between the outer surface of the thin wire 2 and the foreign matters so as to likely reduce a corrosion-resistant property.

On the contrary, with the outer surface of the thin wire 2 electrolytically polished, oxidized scales are removed from the thin wire 2 to restore an original concentration of chromium component of the thin wire 2 so as to resultantly improve the corrosion-resistant property.

As apparent from the foregoing description, the subject method of making a metallic thin wire enables the artisans to mass produce one single metallic thin wire with a high rotation-following capability and high linearity (straightness) provided. The one single metallic thin wire has such good properties as to be appropriately applicable to main constituents of high quality medical tools. This effectively enhances the quality and the performance of the medical tools depending on their usage so as to improve remedial skills and an efficiency of the medical treatment.

It is to be noted that the primarily and secondarily twisting procedures are combined to form a unitary set, and the unitary set is repeatedly applied to the one single metallic thin wire in a plurality of times.

Only the primarily twisting procedure may be applied to the one single metallic thin wire without the secondarily twisting procedure.

Metallic object to be primarily and secondarily twisted is not merely confined to the one single metallic thin wire but also a wire-stranded hollow tube in which the secondarily twisting turns is one time the primarily twisting turns or less than that. In this instance, the wire-stranded hollow tube is primarily twisted in the same direction in which the wire-stranded hollow tube was stranded.

Not only the austenitic stainless steel but other metallic material may be applied to the one single metallic thin wire. After the end of the heat treatment, the electrolytic polishing procedure may be omitted.

The metallic thin wire may be used to not only the guide wire and balloon catheter but also an endscope treating tool, flexible type endscope and the like. The metallic thin wire may be used to an actuation thin wire which requires the superior rotation-following capability except for the medical tool.

What is claimed is:

1. A method of making a metallic thin wire comprising steps of:

preparing one single metallic thin wire having a predetermined length with one end of said one single metallic thin wire as a fixed portion;

primarily twisting said one single metallic thin wire in one direction, and then secondarily twisting said primarily twisted one single metallic thin wire opposite to the direction in which said one single metallic thin wire is primarily twisted, while at the same time, applying a tensile weight to said one single metallic thin wire in the lengthwise direction; and processing said one single metallic thin wire with a heat treatment concurrent or after secondarily twisting in the opposite direction to remove a residual stress from said one single metallic thin wire and producing a thin wire of enhanced torsional rigidity.

2. The method of making a metallic thin wire according to claim 1, wherein said primarily twisting step is an excessive enough to induce slip lines on an outer surface of said one single metallic thin wire.

3. The method of making a metallic thin wire according to claim 1, wherein a total timed amount of said secondarily twisting step is more than 0.15 times inclusive of that of a total timed amount of said primarily twisting step, but less than 1.5 times inclusive of a total timed amount of that of said primarily twisting step.

4. The method of making a metallic thin wire according to claim 1, wherein said primarily twisting step and said secondarily twisting step are combined to form a unitary set, and said unitary set is repeatedly applied to said one single metallic thin wire in a plurality of times.

* * * * *